United States Patent

Godwin et al.

[11] Patent Number: 5,698,747
[45] Date of Patent: Dec. 16, 1997

[54] ESTER-FREE ETHERS

[75] Inventors: Allen David Godwin, Seabrook, Tex.; Georges Marie Karel Mathys, Bierbeek, Belgium

[73] Assignee: Exxon Chemical Patents Inc., Houston, Tex.

[21] Appl. No.: 193,202

[22] PCT Filed: Aug. 14, 1992

[86] PCT No.: PCT/EP92/01875

§ 371 Date: Apr. 12, 1994

§ 102(e) Date: Apr. 12, 1994

[87] PCT Pub. No.: WO93/04028

PCT Pub. Date: Mar. 4, 1993

[30] Foreign Application Priority Data

Aug. 16, 1991 [EP] European Pat. Off. .............. 91307574

[51] Int. Cl.$^6$ ................................................ C07C 41/00
[52] U.S. Cl. ........................................................ 568/699
[58] Field of Search ........................... 568/699, 698

[56] References Cited

U.S. PATENT DOCUMENTS 4,230,892  10/1980  Pruckmayr .......................... 568/617

FOREIGN PATENT DOCUMENTS

170076 A1   2/1986   European Pat. Off. .
391251 A1  10/1990   European Pat. Off. .

OTHER PUBLICATIONS

Perron et al., Bulletin De L Societe Chemique de France, p. 334, col. 1, line 17—col. 2, 1949.

Primary Examiner—Marianne M. Cintins
Assistant Examiner—Dwayne C. Jones
Attorney, Agent, or Firm—Richard D. Jordan; John J. Mahon

[57] ABSTRACT

Ethers, for example those produced by acid-catalyzed dehydration of alcohols, are freed from esters by treatment with an alkoxide, and are especially suitable as drilling fluid components.

8 Claims, No Drawings

ESTER-FREE ETHERS

This application is a 371 of PCT/EP92/01875 filed Aug. 14, 1992.

This invention relates to ethers, especially to ethers suitable for use in load bearing compositions, e.g., drilling fluids, and to a process for their manufacture.

Drilling of oil or gas wells normally involves the circulation of a fluid through the drill string and out through nozzles in the drill bit, the fluid being returned through the annular passage formed between the drill string and the bore. The fluid cools and lubricates the drill, provides a hydrostatic head to counterbalance pressures, and removes the cuttings from the drill bit. Such fluids are also employed in other areas, for example, geothermal drilling, drilling for water and scientific drilling.

Oil-containing drilling emulsions have been used for many years for these purposes. The emulsions may be in the form of a water-in-oil or an oil-in-water emulsion, in each case normally having finely divided solids suspended therein, and containing a variety of additives for various purposes, e.g., emulsifiers, surfactants, pH control agents, biocides, corrosion inhibitors, weight an viscosity regulators, oxygen and sulphur scavengers, and fluid-loss additives.

The oil traditionally used was a hydrocarbon oil, often with an aromatic content; concern for the environment has recently required hydrocarbon oils used for the purpose to be largely aliphatic and more recently, because aliphatic hydrocarbons are not readily biodegradable, hydrocarbons are being increasingly restricted in their use. Many replacements for hydrocarbons have been suggested; these have primarily been aliphatic materials with functional groups that facilitate biodegradation, for example, ester groups. Esters are, however, likely to be saponified in use, causing odour, viscosity and caking problems in the drilling fluid.

In our co-pending European Patent Application No. (Case 91PINT008), we describe drilling fluids in which the oil phase comprises certain aliphatic ethers, which in one embodiment are derived from an alcohol obtained by hydroformylating an olefin feedstock and hydrogenating the resulting aldehyde. The alcohol is converted to an ether over an acid catalyst, and such a manufacturing process produces an ether containing ester impurities as a result of reaction between the alcohol and the acid catalyst. The esters can hydrolyse during use and cause degradation of the drilling fluid.

When acid catalyst are used in ether synthesis as described above, the catalyst is neutralized after completion of the reaction by sodium hydroxide or carbonate, followed by washing with water to remove the organic and inorganic salts formed. This procedure at best only partially hydrolyses the residual esters present and, to obtain ester-free ethers, the product must be distilled. With certain catalysts, however, the ester is not completely separated from the ether even by distillation.

There accordingly remains a need for a process for removing ester contaminants from an ether obtained by acid catalysed conversion of an alcohol.

The present invention provides a process for removing an ester impurity from an ether which comprises treating the ester-ether mixture with a metal salt of an alcohol.

The present invention also provides a process for the manufacture of an ether by acid-catalysed reaction of at least one alcohol wherein after reaction the ether-containing reaction mixture is treated with a metal salt of an alcohol.

The metal is advantageously an alkali or an alkaline earth metal, preferably sodium or potassium.

The metal salt is advantageously a salt of a monohydric alcohol, e.g., an alkanol, preferably an alkanol having 1 to 6, especially 1 to 4 carbon atoms, for example ethanol, propanol, butanol, pentanol or hexanol, but advantageously methanol. (The salt may be a salt of the alcohol that has been converted to the ether.) Of alcohols having isomers, the primary isomer is preferred.

The metal salts of alcohols are referred to subsequent herein for brevity as alkoxides.

The purification process is effective to remove unwanted esters however formed, but is especially suitable for removing esters formed by unwanted side reactions with an acid catalyst, especially sulphonic acid esters, for example, the esters of methane, trifluoromethane, and toluene sulphonic acids, or of chloracetic, trifluoroacetic, or sulphuric acids.

The quantity of alkoxide employed will depend on the concentration of the ester impurity which in turn will be related to acid catalyst concentration. A molar excess of alkoxide is advantageously employed based on the ester content of the material. Advantageously alkoxide is used in a proportion in the range up to 2.5 times the molar quantity of ester.

The alkoxide is advantageously added to the reaction mixture in liquid form, preferably in the form of a solution in the corresponding alcohol.

The reaction time is advantageously in the range of from 30 minutes to 4 hours, preferably from 1 to 3 hours, at a temperature advantageously in the range of from room temperature to 100° C., preferably from 55° to 75° C., the higher temperatures corresponding to shorter times.

After reaction, the product is washed with water, to remove the acid catalyst and the metal salt of the acid. Unreacted alcohol and any olefin formed as a by-product of the dehydration are removed by distillation, leaving purified ether.

The purification process is applicable to all ethers, especially those derived from alcohols having 4 or more carbon atoms, provided that there are no other functional groups on the molecule that would react with alkoxide. Symmetrical or unsymmetrical ethers of aliphatic alcohols having from 4, especially 6, to 14 carbon atoms, more especially from 8 to 12, and particularly 9 or 10, carbon atoms, are especially suitable for purification by the process of the invention.

While the applicants do no wish to be bound by any theory of operation of the invention, it is believed that the alkoxide reacts with the ester which after water treatment forms a metal salt of the acid moiety of the ester, together with an alcohol of the ester and of the alkoxide, for example:

The ester-free product is suitable for use as the oil phase in drilling fluids, and the present invention accordingly provides a drilling fluid comprising a substantially ester-free aliphatic ether having from 16 to 26 carbon atoms, advantageously a di-iso-nonyl or di-iso-decyl ether. The invention also provides the use of a substantially ester-free aliphatic ether as a component of a drilling fluid, advantageously a di-iso-nonyl or di-iso-decyl ether.

The following Examples, in which percentages are by weight unless otherwise indicated, illustrate the invention: 1462 g of iso-decyl alcohol (mixture of isomers, obtained from a hydroformylated and hydrogenated $C_9$ olefin feedstock) and 37.5 g of methane sulphonic acid (2.56% by weight on alcohol) were charged under nitrogen into a reactor equipped with a Dean-Stark trap and condenser, and heated with stirring for 30 minutes until a temperature of 220° C. was reached. The reaction mixture was maintained at that temperature for 5 hours 20 minutes, the water formed being removed. Analysis of a sample of the product indicated 92.4% conversion of alcohol.

After cooling the reaction mixture to 70° C., 79 g of a 30% by weight methanolic solution of sodium methoxide were added and the temperature maintained at 65° C. for 2 hours 30 minutes. The produce was washed twice, each time with 280 g of water at 65° C. for 30 minutes, to remove sodium methane sulphonate and methane sulphonic acid, and then stripped at 160° C. to 200° C., 100 to 50 mm Hg (=13 to 6.3 kPa), to remove decenes and unreacted alcohol. The NMR spectrum and gas chromatographic (GC) analysis showed no trace of methane sulphonic ester. Detailed results are shown in the Table following Example 8.

EXAMPLE 2

246 g of crude reaction mixture obtained by a procedure similar to that described in Example 1 and containing 4.2% decenes, 7.7% iso-decyl alcohol, 85.3% di-iso-decyl ether, and 2.9% of methane sulphonic iso-decyl esters, were treated with 3.8 g of solid sodium methoxide and stirred vigorously under nitrogen for 2 hours at 100° C. The resulting mixture was water washed as described in Example 1. GC analysis showed that 0.4% of methane sulphonic iso-decyl ester remained.

EXAMPLE 3

Example 2 was repeated, except that the reaction with sodium methoxide was carried out at 150° C. GC analysis indicated 0.2% of residual ester.

Examples 2 and 3 show that the addition of sodium methoxide in solid form removed most, but not all, of the ester by-product, more severe conditions being required than when a solution of alkoxide is used as in Example 1.

Comparison Example A 160 g of crude reaction mixture obtained as described in Example 1 and containing 4.8% decenes, 13.3% iso-decyl alcohol, 80.5% di-iso-decyl ether, and 2.9% methane sulphonic iso-decyl ester were treated with 40 g of 50% potassium hydroxide solution under nitrogen for 6.5 hours at 100° C. with vigorous stirring. GC analysis showed 1% of residual methane sulphonic iso-decyl ester.

EXAMPLE 4

The procedure of Example 1 was followed, but using n-octyl alcohol as starting material, and carrying out the catalysed etherification at 160° to 185° C. 1.07 moles of sodium methoxide (as a 30% solution in methanol) per mole of methane sulphonic acid were used in the post-treatment of the reaction product. The results are shown in the table following Example 8.

EXAMPLE 5

The procedure of Example 4 was followed, using iso-octyl alcohol as starting material, and etherifying at 165° to 185° C. The results are shown in the table following Example 8.

EXAMPLE 6

The procedure of Example 4 was followed, using n-decyl alcohol as starting material, and etherifying at 180° to 220° C. The results are shown in the table following Example 8.

EXAMPLE 7

The procedure of Example 6 was followed, using a mixture of n- and iso-decyl alcohols. The results are shown in the table following Example 8.

EXAMPLE 8

The procedure of Example 6 was followed, using iso-tridecyl alcohol as starting material, and employing 2.14 moles of sodium methoxide per mole of methane sulphonic acid in the post-treatment. The results are shown in the Table below.

| | Example No. | | | | | |
|---|---|---|---|---|---|---|
| | 1 | 4 | 5 | 6 | 7 | 8 |
| Ester Content, Wt % Before Treatment with MeONa | 2.7 | 2.1 | 0.1 | 2.2 | 2.6 | 3.1 |
| Ester Content, Wt % After Treatment with MeONa | 0.0 | 0.1 | 0.0 | 0.0 | 0.0 | 0.2 |
| Product Composition After Stripping, Wt % | | | | | | |
| Olefins | 0.0 | 0.0 | 0.0 | 0.1 | 0.0 | 0.0 |
| Alcohol | 2.6 | 0.0 | 0.0 | 0.5 | 0.1 | 1.6 |
| Esters | 0.0 | 0.1 | 0.0 | 0.0 | 0.1 | 0.1 |
| Ethers | 97.4 | 99.1 | 100.0 | 99.4 | 99.8 | 98.3 |
| Viscosity cSt, 20° C. (1 cSt = $10^{-6}$ m$^2$/s) | 8.73 | 4.5 | 4.20 | 8.43 | 8.43 | 23.73 |
| Pour Point, °C. | <−42 | −6 | <−42 | 18 | 0 | <−42 |

The results for Example 5 are of limited accuracy because of overlapping of the ester and ether peaks in the GC analysis of the iso-octyl radical.

We claim:

1. A process for removing an ester impurity from an ether product which comprises treating the ester-ether mixture with a metal salt of an alcohol.

2. A process as claimed in claim 1, wherein the metal is an alkali metal.

3. A process as claimed in claim 1, wherein the metal salt is a salt of an alkanol.

4. A process as claimed in claim 1, wherein the ester is a sulphonic acid ester.

5. A process as claimed in claim 1, wherein a molar excess of the metal salt is employed in a range up to 2.5 times, based on the ester content.

6. A process as claimed in claim 1, wherein the ester-ether mixture is treated for a time in the range of from 30 minutes to 4 hours at a temperature in the range of from room temperature to 100° C.

7. A process as claimed in claim 1, wherein the metal salt is added to the mixture containing ether and ester in liquid form.

8. A process as claimed in claim 1, wherein the ether is an ether of one or more aliphatic alcohols having 4 to 14 carbon atoms.

* * * * *